United States Patent
Thomas et al.

(10) Patent No.: US 10,743,961 B2
(45) Date of Patent: Aug. 18, 2020

(54) DEVICE FOR SURGICAL ASSISTANCE

(71) Applicants: Varghese Thomas, Kottayam (IN); P. S. John, Kottayam (IN); Jibin Jose, Thrissur (IN); Geo Paul Elamkunnapuzha Illikkal, Trichur (IN)

(72) Inventors: Varghese Thomas, Kottayam (IN); P. S. John, Kottayam (IN); Jibin Jose, Thrissur (IN); Geo Paul Elamkunnapuzha Illikkal, Trichur (IN)

(*) Notice: Subject to any disclaimer, the term of this patent is extended or adjusted under 35 U.S.C. 154(b) by 0 days.

(21) Appl. No.: 16/233,571

(22) Filed: Dec. 27, 2018

(65) Prior Publication Data

US 2019/0201162 A1  Jul. 4, 2019

Related U.S. Application Data

(60) Provisional application No. 62/628,375, filed on Feb. 9, 2018.

(51) Int. Cl.
| | |
|---|---|
| *A61B 90/57* | (2016.01) |
| *A61G 13/12* | (2006.01) |
| *A61G 13/10* | (2006.01) |
| *A61G 13/00* | (2006.01) |

(52) U.S. Cl.
CPC ............ *A61B 90/57* (2016.02); *A61G 13/101* (2013.01); *A61G 13/1235* (2013.01); *A61B 2090/571* (2016.02); *A61G 13/0045* (2016.11)

(58) Field of Classification Search
CPC A61B 90/57; A61B 2090/571; A61G 13/101; A61G 13/1235; A61G 13/0045

USPC .................................................. 600/227–231
See application file for complete search history.

(56) References Cited

U.S. PATENT DOCUMENTS

| | | | | | |
|---|---|---|---|---|---|
| 3,762,401 | A | * | 10/1973 | Tupper | A61B 17/02 600/217 |
| 6,023,800 | A | * | 2/2000 | Stickley | A61G 7/0507 248/229.26 |
| 6,387,047 | B1 | * | 5/2002 | Duhaylongsod | A61B 17/0281 600/228 |
| 9,850,924 | B2 | * | 12/2017 | Vogtherr | A61G 13/101 |
| 2005/0215865 | A1 | * | 9/2005 | LeVahn | A61B 17/0206 600/231 |
| 2006/0272979 | A1 | * | 12/2006 | Lubbers | A61B 17/02 206/557 |
| 2009/0169831 | A1 | * | 7/2009 | Malcolm | A61G 13/101 428/192 |
| 2010/0071128 | A1 | * | 3/2010 | Campagna | A61B 6/0421 5/81.1 R |

(Continued)

*Primary Examiner* — Pedro Philogene
*Assistant Examiner* — David C Comstock

(57) ABSTRACT

A device for surgical assistance is disclosed. The device comprising one or more rails, and a plurality of side posts. The rails are configured to attach to a hand table via one or more engagement members. The plurality of the side post comprises an upper part and a lower part. The lower part of the said side post is engaged to the rails via a clamp mechanism. The upper part of the said side post is configured to hold surgical equipment. Further, each of the side post is height adjustable. The device further comprises a rail extension system, which is attached to an end portion of rails lying close to a trunk portion of the patient.

12 Claims, 14 Drawing Sheets

(56) References Cited

U.S. PATENT DOCUMENTS

| | | | |
|---|---|---|---|
| 2012/0126079 A1* | 5/2012 | Russell | A61G 13/101 248/229.23 |
| 2013/0023735 A1* | 1/2013 | Brown | A61B 17/02 600/229 |
| 2015/0075537 A1* | 3/2015 | DeMayo | A61G 13/124 128/845 |
| 2018/0000666 A1* | 1/2018 | Sirkin | A61G 1/04 |
| 2019/0133862 A1* | 5/2019 | Norris | A61G 13/1235 |

* cited by examiner

DEVICE FOR SURGICAL ASSISTANCE

CROSS REFERENCE TO APPLICATION

This patent application claims the benefit of Indian Provisional patent application 201741047217 filed on Dec. 29, 2017. The above application is incorporated by reference herein in its entirety.

BACKGROUND OF THE INVENTION

A. Technical Field

The invention disclosed herein generally relates to a medical equipment or device. More particularly, the invention disclosed herein relates to a device to provide surgical assistance for performing medical treatment.

B. Description of Related Art

Many emergency room and other surgical operations require a surgeon to operate on a patient's limb or extremity. Upper limb surgeries include orthopedic and plastic surgery procedures. This include fracture fixation (carpal bones/radius/ulna/humerus) and soil tissue procedures (wound management, flap coverage, tendon transfer, tumor excision, carpel tunnel release, etc.). Upper limb surgeries are performed on a hand table, which is an attachment to a standard operating table. A smooth and an effective surgical procedure is performed by fulfilling the following steps: (i) attain haemostasis using electrocautery; (ii) suction of body fluids and smoke produced on using electrocautery; (iii) tissue retraction; (iv) exposure of bone with adequate protection to surrounding soil tissue; and (v) bone holding and fracture reduction [steps (iv) & (v) for orthopedic procedures like fracture fixation]. The surgeon has to take care, while performing the upper limb surgeries. This is because tendons, nerves, and blood vessels are to be meticulously rejoined to assure proper alignment of any lacerated tissues. Further, the use of microsurgical techniques may also be required especially for the hand surgeries.

In the present practice, the upper limb surgery is encountered with various hurdles. The major problem faced to conduct the upper limb surgery is the requirement of the skilled assistants during each step of the surgery. The surgeon should also be equipped with all the equipment necessary for the surgery. The arrangement of these surgical equipment are performed manually with or without a checklist. Moreover, there is no system or arrangement that innately is decorous to ensure the availability of all the necessary surgical equipment for the upper limb surgery. To perform the upper limb surgery, the hand of the patient is positioned on the hand table, in such a manner that the surgeon performing the operation or treatment has an easy access to an intended surgical site. However, maintaining the patients' hand in a desired position is a difficult task, when qualified assistants are not readily available. Control of the position of the patient's hand and lingers during surgery plays a major role in accomplishing a successful surgery.

During orthopedic surgeries for fracture fixation, adequate reduction of the fractured bone fragments is necessary. The fractured hone fragments are displaced in all the three planes due to the pull of the muscles attached to a bone. These deforming forces are to be negotiated and the misalignment of the hone fragments must be corrected before performing the fracture fixation with various fixation methods. This is possible for the surgeon by firm hold on the bone fragments with the help of bone clamps. Once the fracture is reduced, and aligned by the surgeon, a stainless steel or titanium plate should be placed on the bone across the fracture site, which will be fixed with screws. The bone clamps need to be loosened or adjusted by the surgeon to facilitate the placement of the plate across the fracture. However, while doing so there is always a chance for the fracture to be displaced again. The reoccurrence of the displacement increases the work burden on the surgeon, as the surgeon needs to realign the fracture again and manually maintain it until the surgeon could negotiate the plate across the reduced fracture. The surgeon also has to confirm that the fracture reduction is maintained while inserting the screws through the plate and fixing the bone. The aforementioned steps are performed manually and need assistance by skilled work force.

An existing prior art U.S. Pat. No. 5,578,032A has a provision of maintaining fracture reduction. However, it does not have a provision to permit independent movement of each bone clamp separately, which is essential for correcting misalignment in various planes. It also does not provide the provision for a plate positioning or plate holding mechanism.

An existing prior art, US20060272979 A1 assigned to Lubbers Lawrence and et al. describes a tray used for operations on a patient's limb or extremity attached to an operation table with any locking mechanism. The surgical tray comprises a height-adjustable post member used to attach the retention & retraction devices such as surgical stays and provisions for attaching other surgical instruments such as scissors, syringe, irrigator, etc.

Henceforth, there is a need for a device that helps in reducing the workload encountered by the surgeons, when attempting to operate on the patient's limb or extremity. Further, there is the need for a device that addresses the aforementioned problems, and provides a precise surgical assistance without any need of skilled work force for assistance.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

In an embodiment, a device for surgical assistance is disclosed. The device comprises a rail system having one or more attachable rails. The attachable rails are removably attached to a hand table via one or more clamps. The hand table is adapted to support a portion of a user's body. The device further comprises a plurality of side posts, each side post comprising an upper part and a lower part. The lower part of the side post is engaged to the attachable rails via one or more spring lock clamps, configured to move along the attachable rail as desired by a surgeon. The upper past of the said side posts are configured to hold one or more surgical equipment including a tissue retraction system, a self-retaining bone lever assembly, an electrocautery tip and a vacuum suction tip, required for performing a surgery.

The spring lock clamp comprises a ball bearing surface. The hall hearing surface is interlaced with the attachable rail for reducing friction and permits free gliding of the side posts over the attachable rail. The attachable rail comprises a slot to accommodate the spring lock clamp. The spring lock clamp further enables a longitudinal movement of the side posts over the attachable rail. The longitudinal movement of the side posts over the attachable rail is controlled via a slide lock system. In one embodiment, the side posts are height adjustable. In one embodiment, the attachable rail and side posts are retrofittable to any existing hand table.

In one embodiment, the upper part of the side post comprises a first slot and a second slot. The first slot comprises a concave surface, configured to receive a beaded wire. The beaded wire is engaged to a bone lever holder of the self-retaining bone lever assembly. The second slot comprises an auto-lock mechanism, configured to hold a retractor handle of the tissue retraction system. In another embodiment, the upper part of the side post comprises a multi axial clamp or poly axial clamp, for the self-retaining bone lever assembly. In yet another embodiment, the upper part of the side post comprises a socket and a recoil console, for the electrocautery tip or the vacuum suction tip. In yet another embodiment, the upper part of the side post is modifiable such that various surgical equipment could be held by the side posts. The device further comprises a rail extension system, attached to the rail on either side of the hand table.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing summary, as well as the following detailed description of the invention, is better understood when read in conjunction with the appended drawings. For illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present invention will now be given with reference to the Figures. It is expected that the present invention may be embodied in other specific Forms without departing from its spirit or essential characteristics. The described embodiments are to be considered in all respects only as illustrative and not restrictive.

Figure 1A:
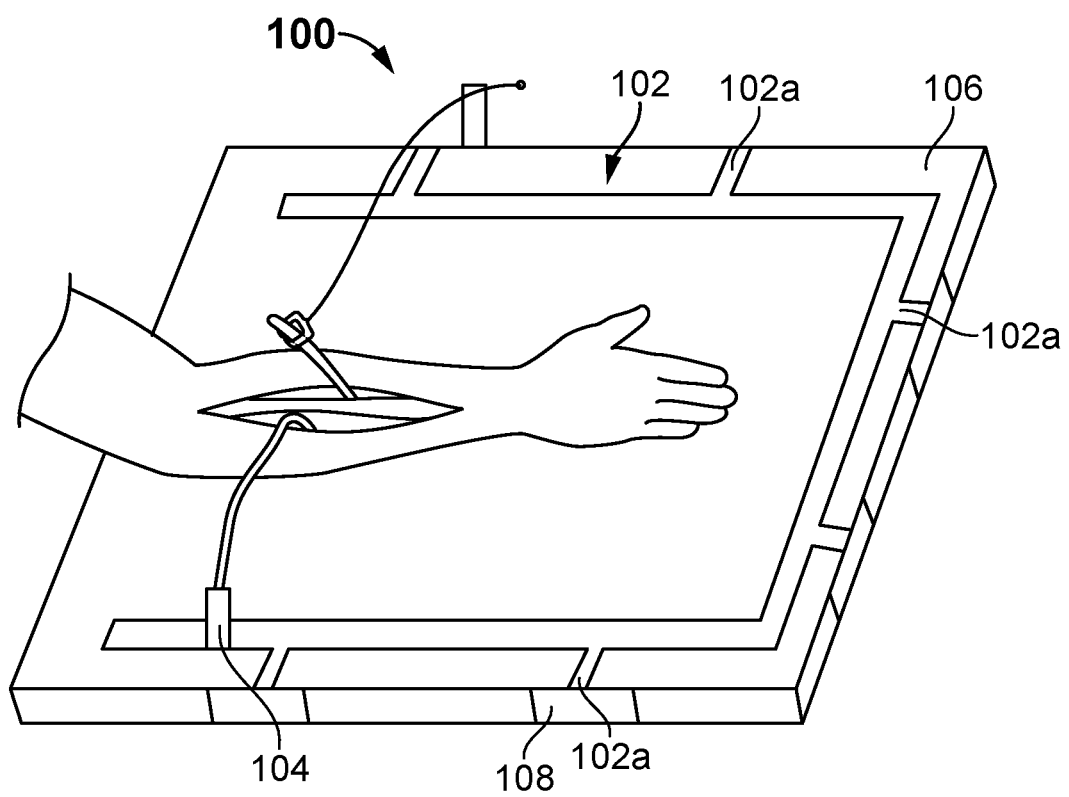
FIG. 1A exemplarily illustrates a top view of a device, according to an embodiment of the present invention.
Figure 1B:
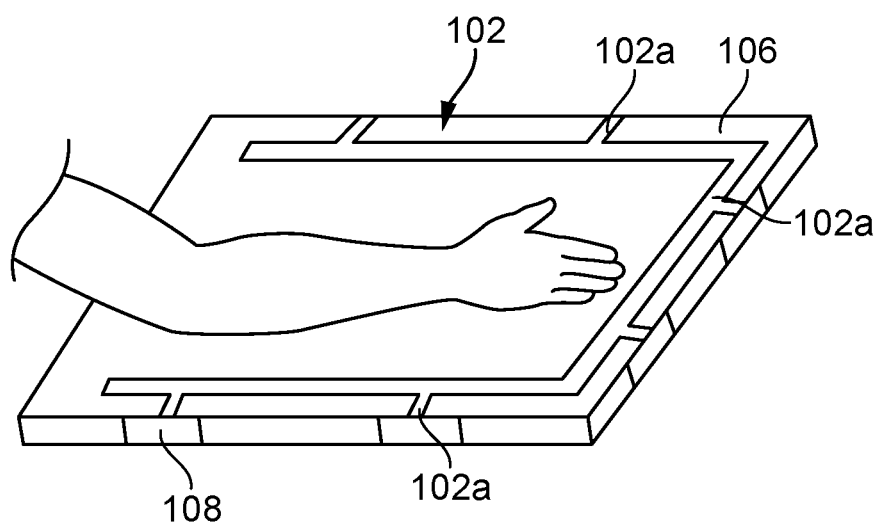
FIG. 1B exemplarily illustrates an engagement of a rail system to a hand table, according to an embodiment of the present invention.

FIG. 1A exemplarily illustrates a top view of the device 100 according to an embodiment of the present invention. The device 100 is a surgical assistance device configured to engage to a hand table 106, wherein the device 100 helps in well-organized and user-friendly fracture reduction procedure in orthopedic and plastic surgeries. The device 100 is an integrated hand-table extension device. The device 100 comprises a rail system 102, and a plurality or side posts 104. FIG. 1B exemplarily illustrates engagement of the rail system 102 to the hand table 106, according to an embodiment of the present invention. In an embodiment, the rail system 102 of the device 100 comprises one or more rails 102a. In another embodiment, the rail system comprises at least three rails 102a. The rail system 102 is rigidly fixed to the hand table 106, wherein the hand table 106 is adapted to support a portion of a patient's body. The rail system 102 is attached to the hand table 106 in a manner that it provides a pathway for the patient for placing a limb or extremity on the hand table 106. The rails 102a are fixed to the hand table 106 via one or more engagement members 108. The engagement members 108 is, for example, one or more clamps, a clamp system, etc. The device 100 could be attached to any surgical table adapted to receive the portion or the patient's body not limited to, limbs. The rail system 102 is removably secured to the hand table 106.

Figure 2:
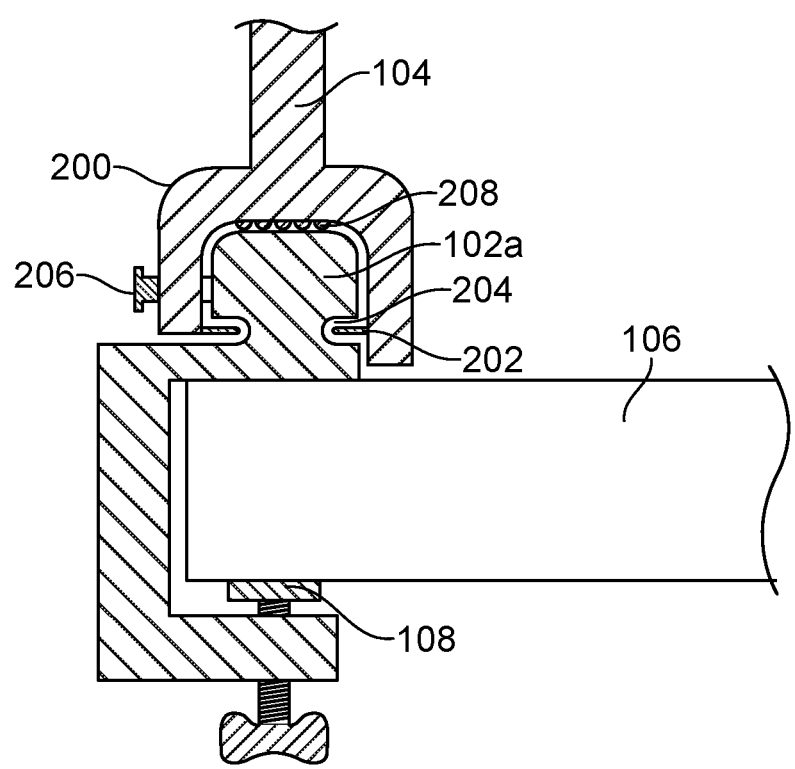
FIG. 2 is a cross sectional view illustrating an engagement of a side post to a rail according to an embodiment of the present invention.

Referring to FIG. 2, a cross sectional view of an engagement of the side post 104 to the rail 102a, is illustrated, according to an embodiment of the present invention. In an embodiment, each of the side posts 104 comprises an upper part and a lower part. The lower part of the side post 104 is affixed to the rails 102a via a clamp mechanism 200. The clamp mechanism 200 comprises a spring lock clamp or relative spring lock clamp mechanism 202. A slot 204 on the rail 102a is configured to accommodate the spring lock clamp 202. The spring lock clamp 202 allows a longitudinal movement of the side post 104 over the rail 102a. The release of spring lock clamp 202 enables a slidable longitudinal movement for positioning the side post 104 over the rail 102a as required by the user. The longitudinal movement of the side post 104 is controlled via a slide lock system 206. The clamp mechanism or clamp 202 has a ball bearing surface 208, which interface with the rail 102a for reducing friction, and permits a free gliding of the side post 104 over the rail 102a. The side-posts 104 are attached to the rail 102a with ease, and the rotation locks engage automatically. The rails 102a and the side post 104 could be independently fixed to any existing hand table.

Figure 3A:
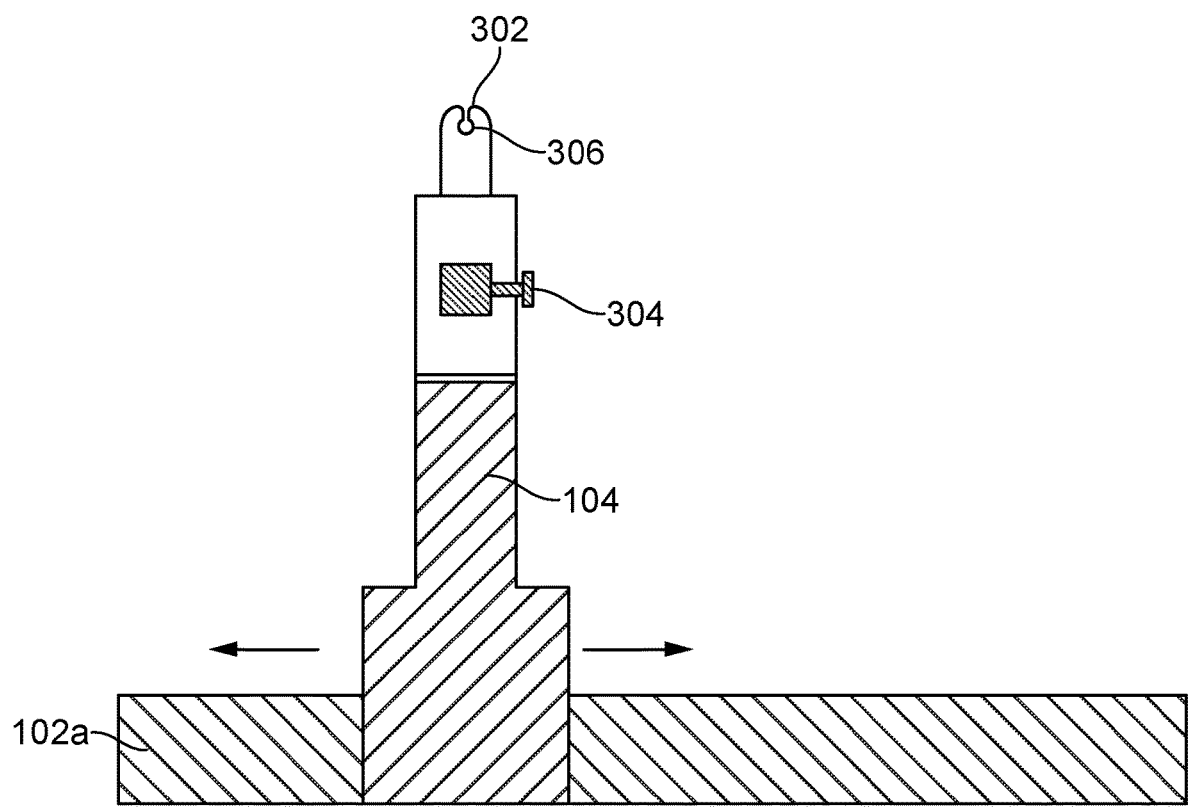
FIG. 3A exemplarily illustrates a first slot and a second slot provided on an upper part of the side posts, according to an embodiment of the present invention.

In an embodiment, the upper part of each of the side post 104 has a provision for various attachment such as but not limited to surgical equipment or medical equipment. Each of the side posts 104 is configured to hold various surgical equipment or instruments required for performing a surgery. The surgical equipment held by the side posts 104 are for example but not limited to, a tissue retraction system 300, a self-retaining bone lever assembly 400, electrocautery tip 600, and vacuum suction tip 602 among others. Further, each of the side posts 104 is height adjustable. Referring to FIG. 3A, a first slot 302 and a second slot 304 provided on the upper part of the side posts 104, is illustrated, according to an embodiment of the present invention. In an embodiment, the upper part of the side post 104 comprises the first slot 302; and the second slot 304. A concave surface 306 on the first slot 302 is configured to receive a beaded wire 404 (shown in FIG. 4). The tissue retractor system 300 comprises a handle 308, received or held by the second slot 304, wherein the second slot 304 has an auto lock mechanism. In alternate embodiments, the upper part of the side post 104 comprises a multi axial clamp or poly axial clamp 504 (shown in FIG. 5). In some embodiments, the upper part of the side post comprises a socket 606, and a recoil console 604 (shown in FIG. 6B and FIG. 6C). The upper part of the side posts 104 is modified such that the surgical equipment of various sizes, dimensions, and design are hold by the side posts 104 of the device 100.

Figure 3B:
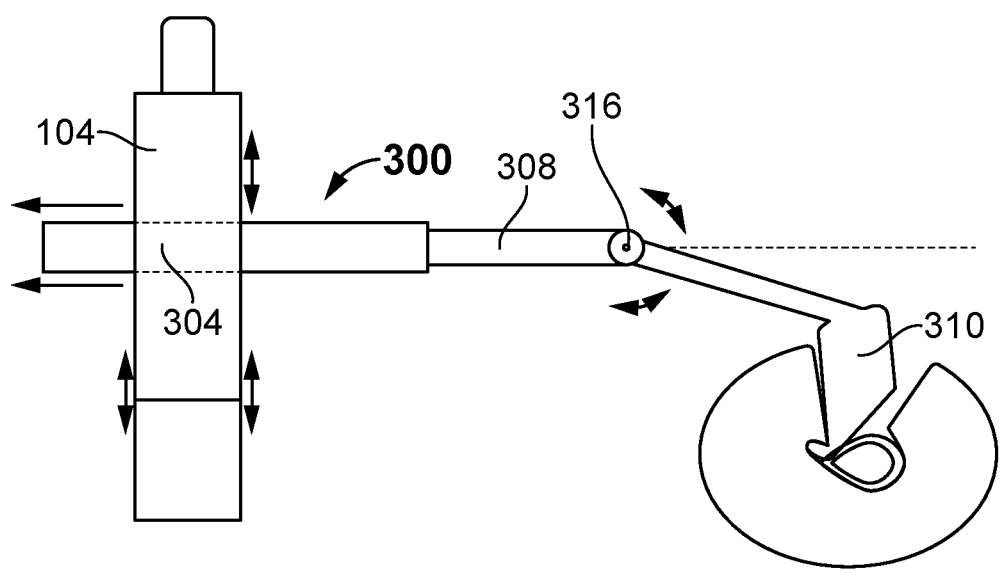
FIG. 3B exemplarily illustrates the side post holding a tissue retraction system, according to an embodiment of the present invention.
Figure 3C:
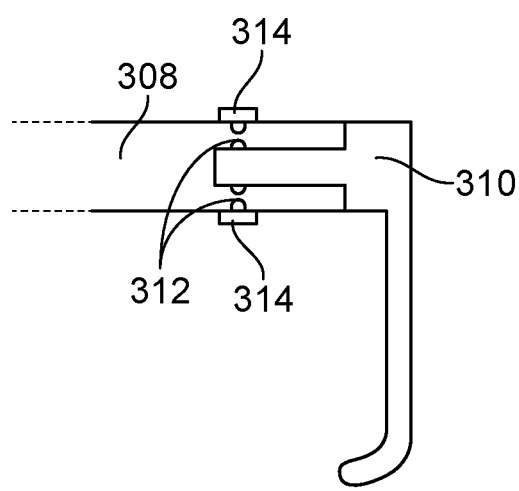
FIG. 3C exemplarily illustrates a mechanism of interchanging a retractor blade of the tissue retractor system, according to an embodiment of the present invention.
Figure 3D:
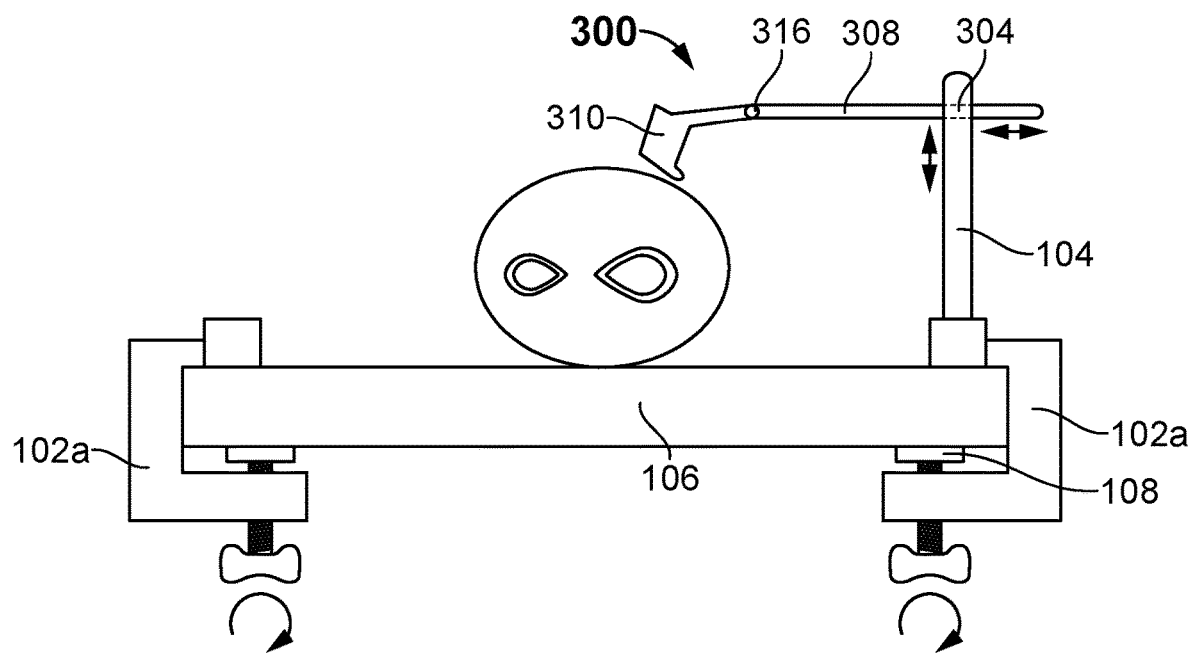
FIG. 3D is a front view illustrating implementation of the device on the hand table to perform surgery, according to an embodiment of the present invention.

Referring to FIG. 3B, the side post 104 holding the tissue retraction system 300, is illustrated, according to an embodiment of the present invention. The tissue retractor system 300 comprises the retractor handle 308, and a retractor blade 310. A proximal end of the retractor handle 308 is inserted into the second slot 304 having the auto lock mechanism. The amount of retraction force is controlled at the retractor handle 308, and the side post 104 interface joint. The retraction handle 308 has a hinge joint 316 configured to regulate an angle of retraction. Further, the height of the tissue retraction system 300 is adjusted at the side post 104. In an embodiment, the retractor blade 310 used in the tissue retraction system 300 is of different sizes. Referring to FIG. 3C, a mechanism of interchanging the retractor blade 310 of the tissue retractor system 300, is illustrated, according to an embodiment of the present invention. A distal end of the retractor handle 308 includes a blade socket. The blade socket facilitates in interchanging the retractor blade 310 of different sizes. The retractor blade 310 is pushed into the blade socket with an auto-lock system 312 to retain the retractor blade 310. A lock release bottom 314 provided in the auto lock system 312 enables the release of the retractor blade 310 from the blade socket. Referring to FIG. 3D, a front view of the device 100 implemented on the hand table 106 to perform surgery, is illustrated, according to an embodiment of the present invention. The hand table 106 is adapted to support the portion of the patient's limb to be operated. FIG. 3D illustrates the tissue retraction system 300 hold by the side post 104 of the device 100, wherein the tissue retraction system 300 is in use to retract the tissues of the portion of the patient's limb to be operated.

Figure 4:
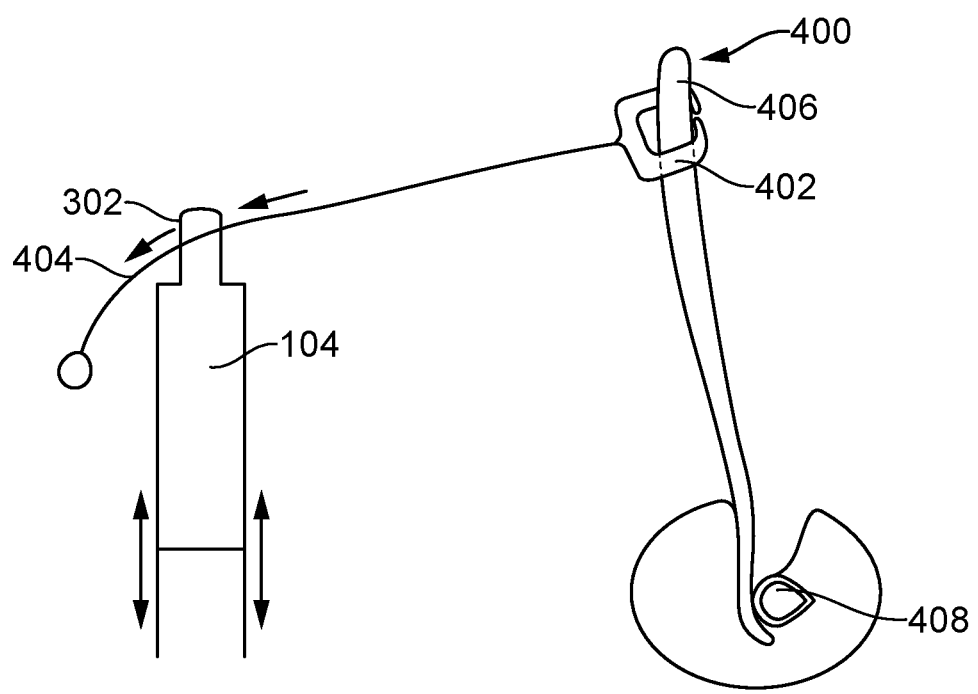
FIG. 4 exemplarily illustrates the side post holding a self-retaining bone lever assembly having a plate positioning mechanism, according to an embodiment, of the present invention.

Referring to FIG. 4, the side post 104 holding the self-retaining bone lever assembly 400, is illustrated, according to an embodiment, of the present invention. The self-retaining bone lever assembly 400 comprises a bone lever holder 402, and the beaded wire 404. The beaded wire 404 is, but not limited to a steel beaded wire. The bone lever holder 402 is configured to hold a bone lever 406. The bone lever holder 402 is engaged to the steel beaded wire 404, which is further engaged to the side post 104. The steel beaded wire 404 is locked to the side-post 104 at the first slot 302, and the amount of traction force applied on the bone lever 406 is thereby controlled. The bone lever 406 hold by the bone lever holder 402 is used to treat all exposed bone 408. In another embodiment, the bone lever 406 is also hold by the bone lever assembly 400 provided to the different side-posts 104, for better stability of the bone lever 406, if required.

Figure 5:
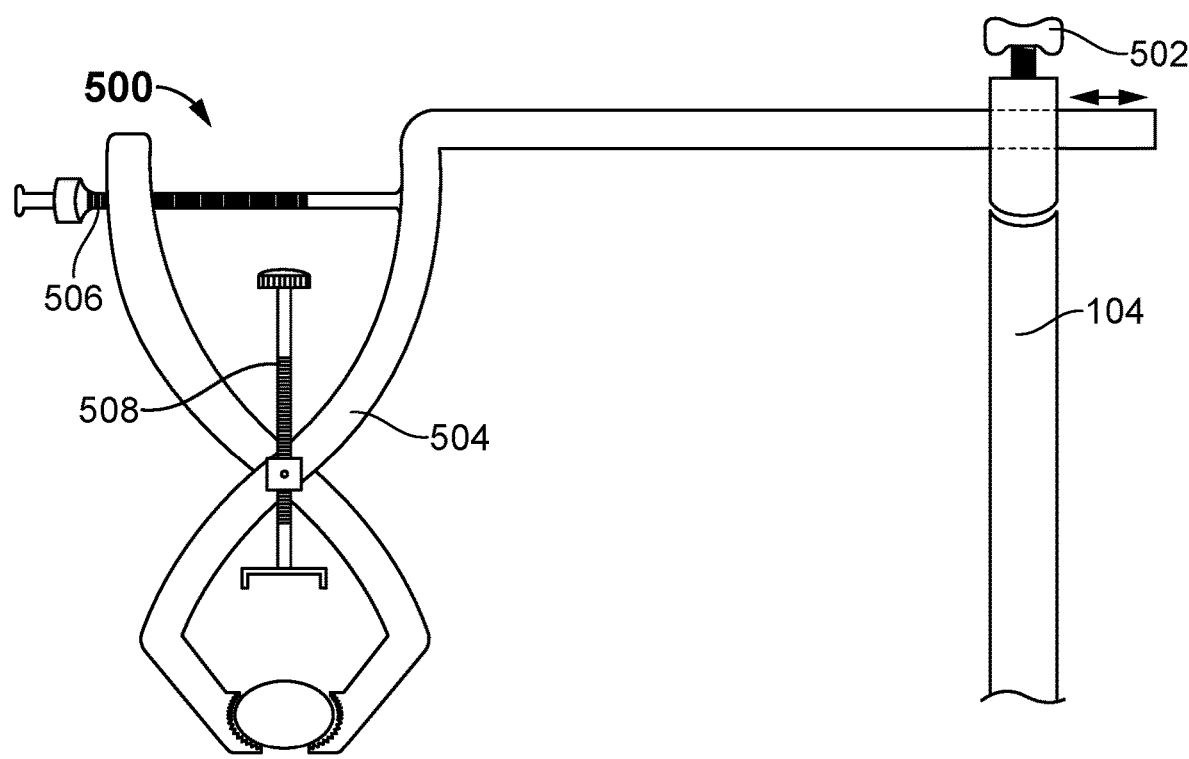
FIG. 5 exemplarily illustrates the side post holding a self-retaining bone clamp assembly having a plate positioning mechanism, according to an embodiment of the present invention.

Referring to FIG. 5, the side post 104 holding a self-retaining bone clamp assembly 500 having a plate positioning mechanism 508, is illustrated, according to an embodiment of the present invention. In an embodiment, the upper part of the side post 104 comprises the multi axial clamp or poly axial clamp 502. The poly axial clamp 502 on the side post 104 is configured to hold the self-retaining bone clamp assembly 500. The bone clamp assembly 500 comprises at least a pair of bone clamps 504, a locking mechanism 506 and the plate positioning mechanism 508. The pair of bone clamps 504 are hold together via a locking mechanism 506. The locking mechanism 506 is for example a screw locking mechanism, which facilitates the extension of the pair of bone clamps 504 accordingly, based on the size of the bone to be treated. The screw locking mechanism 506 helps in maintaining firm hold on the bone to be treated. The distance between the pair of bone clamps 504 could be adjusted, even when the bone clamp assembly 500 is engaged to the side post 104 via the multi axial clamp 502. The multi axial clamp 502 upon receiving the bone clamp assembly 500 is locked at the side posts 104. The locking of the bone clamp assembly 500 to the side post 104 permits a surgeon to slide a plate across the fracture via a plate positioning mechanism 508, without disassembling or loosening the bone clamps 504. The clamps 504 are provided with a provision of the plate positioning mechanism 508, which holds the plate flush to the bone once engaged. The present configuration of the self-retaining bone clamp assembly 500 provides a surgical field with the fracture well reduced, and plate positioned suitably for fracture fixation, without the need for ally assistance. Therefore, the surgeon could comfortably proceed with the fracture fixation procedure without the need for any assistance.

Figure 6A:
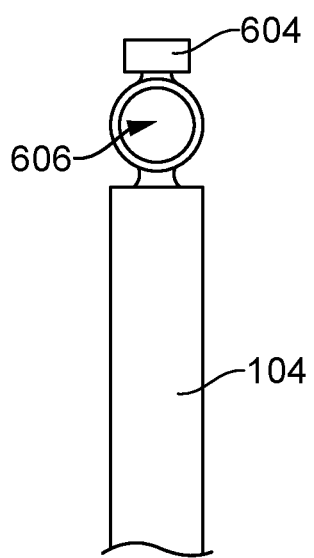
FIG. 6A exemplarily illustrates a recoil mechanism according to an embodiment of the present invention.
Figure 6B:
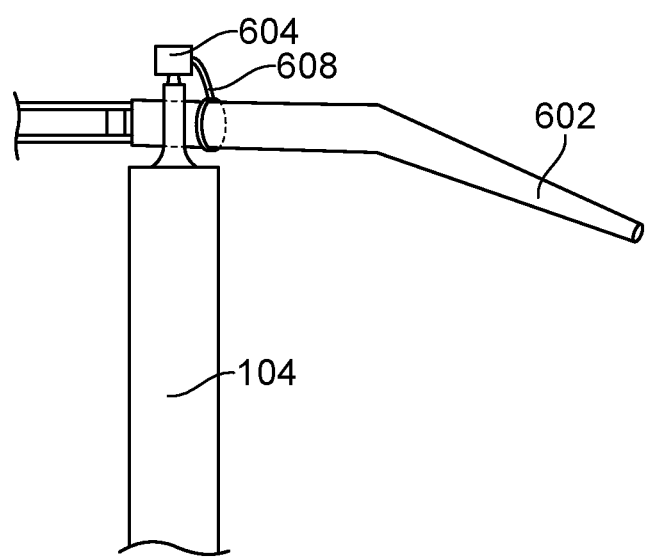
FIG. 6B exemplarily illustrates the side post holding a vacuum suction tip, according to an embodiment of the present invention.

Referring to FIG. 6A, the recoil mechanism is illustrated, according to an embodiment of the present invention. The upper part of the side post 104 comprises a socket 606 and a recoil console 604, The electrocautery tip 600 or the vacuum suction tip 602 rest or seat on the socket 606 located on the upper part of the side post 104. Referring to FIG. 6B, the side post 104 holding the vacuum suction tip 602 is illustrated, according to an embodiment of the present invention. The socket 606 incorporates the recoil console 604. The recoil mechanism comprises the recoil console 604, and an elastic recoil attachment 608. The elastic recoil attachment 608 is configured to attach to the vacuum suction tip 602. The recoil mechanism ensures a smooth and an automatic return of the vacuum suction tip 602 after use.

Figure 6C:
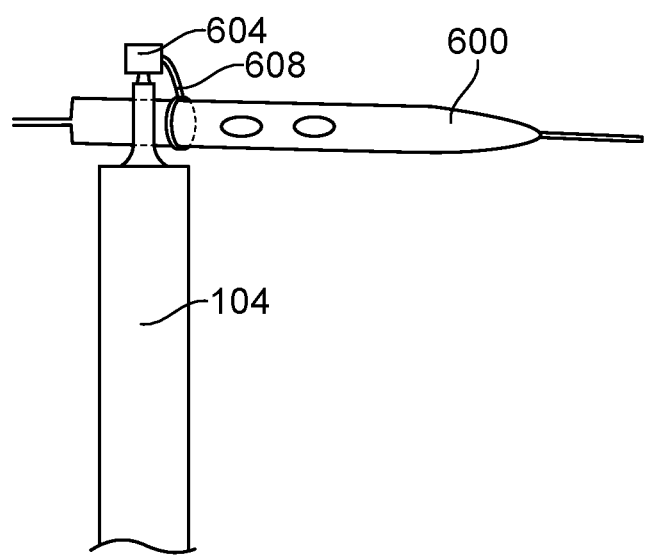
FIG. 6C exemplarily illustrates the side post holding an electrocautery tip, according to an embodiment of the present invention.

Optionally, the recoil function is suspended with the help of a lock system at the recoil console 604. Referring to FIG. 6C, the side post 104 holding the electrocautery tip 600 is illustrated, according to an embodiment of the present invention. The recoiling mechanism for the vacuum section tip 602 is also applicable for the electrocautery tip 600.

Figure 7A:
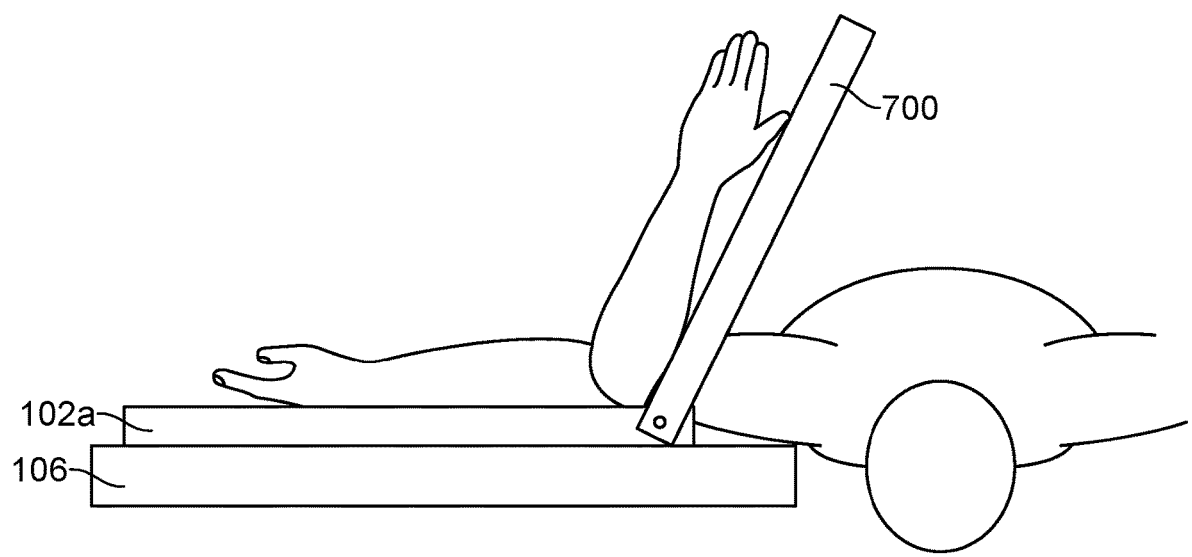
FIG. 7A exemplarily illustrates a top view of a rail extension system, according to an embodiment of the present invention.
Figure 7B:
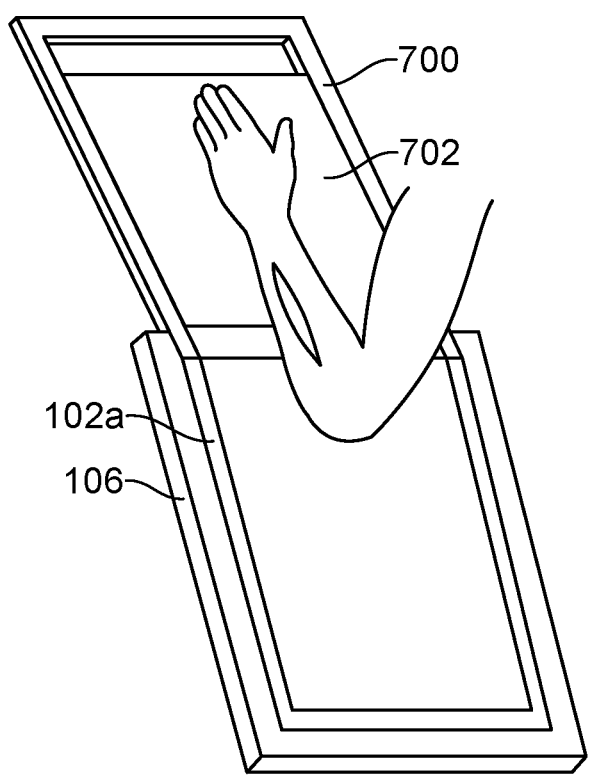
FIG. 7B exemplarily illustrates a view of the rail extension system from a head end of a patient, according to an embodiment of the present invention.

Referring to FIG. 7A, a top view of a rail extension system 700, is illustrated, according to an embodiment of the present invention. The rail extensions system 700 are attached to the rail 102a on either side of the hand table 106. The rail extension system 700 is attached to an end portion of rails 102a lying close to a trunk portion of the patient. The rail extension system 700 is attached in an angle, that it does not touch the trunk of the patient. Referring to FIG. 7B, a perspective view of the rail extension system 700 from a head end of the patient is illustrated, according to an embodiment of the present invention. A firm platform 702 is attached between the rail extensions system 700. The platform 702 is made of high quality fabric or a light and sturdy material like carbon fiber. The limb of the patient is positioned on to the platform surface, facilitating surgical exposure on the medial border. Finger straps or Chinese finger traps could be used to position the limb. In an embodiment, the attachments of the device 100 could be attached to the rail extension system 700 for carrying out an assistant free surgery.

In an embodiment, the device 100 delivers a precise surgical assistance at each step of surgery. The device 100 enables an assistant free surgery without compromising surgical precision. The use of the device 100 eliminates the need for skilled work force for the smooth conduct of surgeries permitting the surgeon to perform surgery even in centers with limited resources. This device 100 improves the health care system, especially in rural areas or in corporate hospital setup enabling a better distribution and utilization of work force. The cost of the surgery imposed on the patient is reduced due to the less utilization of skilled work force in the surgery, resulting in cost effective surgery. The device 100 provides an easy approach to fracture reduction and fixation with the help of the self-retaining bone clamp assembly 500, resulting convenient procedure for the fracture reduction and fixation in less time. The bone clamp assembly 500 permits the insertion of the plate into the fracture site without removing/loosening the bone clamps 504. The device 100 could be used in any existing hand table, and is not limited to a specific hand table. The device 100 is user friendly as the construction of the device 100 is very simple and cost effective.

The foregoing examples have been provided merely for the purpose of explanation and are in no way to be construed as limiting of the system, disclosed herein. While the system has been described with reference to various embodiments, it is understood that the words, which have been used herein, are words of description and illustration, rather than words of limitation. Further, although the system has been described herein with reference to particular means, materials, and embodiments, the system is not intended to be limited to the particulars disclosed herein; rather, the bee system extends to all functionally equivalent structures, methods and uses, such as are within the scope of the invention. Although there has been shown and described the preferred embodiment of the present invention, it will be readily apparent to those skilled in the art that modifications may be made thereto.

The invention claimed is:

1. A device for surgical assistance, the device comprising: a rail system comprising one or more attachable rails, said attachable rails are removably attached to a hand table via one or more clamps, wherein the hand table is adapted to support a portion of a user's body; and a plurality of side posts, each side post comprising an upper part and a lower part, wherein the lower part of the side post is engaged to the attachable rails via one or more spring lock clamps, configured to move along the attachable rail as desired by a surgeon, and the upper part of the said side posts are configured to hold one or more surgical equipment including a tissue retraction system, a self-retaining bone lever assembly, an electrocautery tin and a vacuum suction tip, required for performing a surgery.

2. The device of claim 1, wherein the spring lock clamp comprises a ball bearing surface, wherein the ball bearing surface is interfaced with the attachable rail for reducing friction and permits free gliding of the side posts over the attachable rail.

3. The device of claim 1, wherein the attachable rail comprises a slot to accommodate the spring lock clamp, said spring lock clamp further enables a longitudinal movement of the side posts over the attachable rail.

4. The device of claim 3, wherein the longitudinal movement of the side posts over the rail is controlled via a slide lock system.

5. The device of claim 1, wherein the side posts are height adjustable.

6. The device of claim 1, wherein the attachable rail and side posts are retrofittable an existing hand table.

7. The device of claim 1, wherein the upper part of the side post comprises a first slot and a second slot.

8. The device of claim 1, wherein the first slot comprises a concave surface, configured to receive a beaded wire, wherein the beaded wire is engaged to a bone lever holder of the self-retaining bone lever assembly.

9. The device of claim 1, wherein the second slot comprises an auto-lock mechanism, configured to hold a retractor handle of the tissue retraction system.

10. The device of claim 1, wherein the upper part of the side post comprises a multi axial clamp or poly axial clamp, for the self-retaining hone lever assembly.

11. The device of claim 1, wherein the upper part of the side post comprises a socket and a recoil console, for the electrocautery tip or the vacuum suction tip.

12. The device of claim 1, further comprises a rail extension system, attached to the rail on either side of the hand table.

* * * * *